United States Patent
Allegrini et al.

(10) Patent No.: US 12,077,484 B2
(45) Date of Patent: Sep. 3, 2024

(54) PROCESS FOR THE SYNTHESIS OF MELPHALAN

(71) Applicant: Indena S.P.A., Milan (IT)

(72) Inventors: Pietro Allegrini, Milan (IT); Andrea Bonetti, Milan (IT); Marco Molinari, Milan (IT); Andrea Gambini, Milan (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 18/320,326

(22) Filed: May 19, 2023

(65) Prior Publication Data

US 2023/0286901 A1 Sep. 14, 2023

Related U.S. Application Data

(62) Division of application No. 17/757,830, filed as application No. PCT/EP2020/087443 on Dec. 21, 2020, now Pat. No. 11,787,761.

(30) Foreign Application Priority Data

Dec. 23, 2019 (IT) .................. 102019000025348

(51) Int. Cl.
C07C 227/20 (2006.01)
(52) U.S. Cl.
CPC ................. *C07C 227/20* (2013.01)
(58) Field of Classification Search
None
See application file for complete search history.

(56) References Cited

U.S. PATENT DOCUMENTS 3,032,584 A  5/1962  Franz et al.

FOREIGN PATENT DOCUMENTS

CN  107935875 A  4/2018
WO  2014191426 A1  12/2014

OTHER PUBLICATIONS

Search Report and Written Opinion of PCT/EP2020/087443 of Mar. 24, 2021.
Tomalia D.A. et al., "The synthesis and reactions of beta-substituted ethyl sulfates", Journal of Heterocyclic Chemistry, vol. 9, No. 4, Aug. 1972, pp. 891-894.

*Primary Examiner* — Sudhakar Katakam
*Assistant Examiner* — Jennifer C Sawyer
(74) *Attorney, Agent, or Firm* — Silvia Salvadori, P.C.; Silvia Salvadori

(57) ABSTRACT

The invention relates to a process for the preparation of Melphalan (4-[bis(2-chloroethyl)amino]-L-phenylalanine of formula (I)

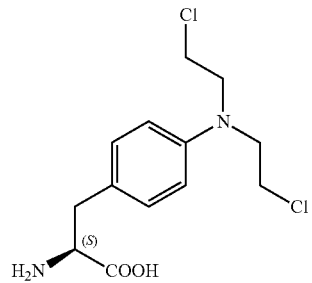

said process comprising the reaction of a 4-amino-L-phenylalanine protected at the carboxy and amino aminoacidic groups with an agent able to convert the aromatic amino group into a group of formula: —$N(CH_2CH_2OS(O)_nO^-)_2$, wherein n is 1 or 2 followed by conversion of the —$N(CH_2CH_2OS(O)_nO^-)_2$ group into a —$N(CH_2CH_2Cl)_2$ group.
The invention also provides novel intermediates useful for the preparation of Melphalan.

3 Claims, No Drawings

PROCESS FOR THE SYNTHESIS OF MELPHALAN

This application is a divisional application of U.S. Ser. No. 17/757,830 filed on Jun. 22, 2022, which is a U.S. national stage of PCT/EP2020/087443 filed on 21 Dec. 2020, which claims priority to and the benefit of Italian Patent Application No. 102019000025348 filed on 23 Dec. 2019, the contents of which are incorporated herein by reference in their entireties.

FIELD OF THE INVENTION

The present invention relates to a synthetic process for the preparation of Melphalan (4-[bis(2-chloroethyl)amino]-L-phenylalanine), currently marketed as hydrochloride salt with the name of Alkeran™.

BACKGROUND OF THE INVENTION

Melphalan, having formula (I)

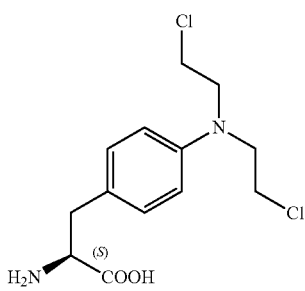

(I)

is a chemotherapy drug belonging to the class of nitrogen mustard alkylating agents. It is able to alkylate the DNA guanine bases and to form stable bonds between the two DNA helices, thus inhibiting DNA replication. Melphalan can be used for the treatment of different neoplasias, such as multiple myeloma, ovarian carcinoma and amyloidosis. Melphalan is also used in the pediatric field for the therapy of retinoblastoma.

U.S. Pat. No. 3,032,584, assigned to National Research Development Corporation, relates to a process for the manufacture of Melphalan which comprises heating a compound of formula:

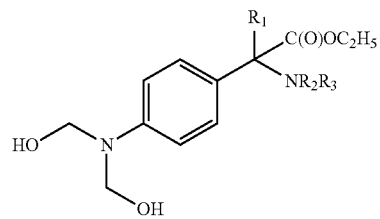

wherein $R_1$ is hydrogen or —COOC$_2$H$_5$, $R_2$ is hydrogen and $R_3$ is a —CHO or —CH$_3$CO group and $R_2$ and $R_3$ together represent a group of formula

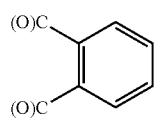

with a chlorinating agent selected from the group consisting of phosphorus oxychloride (POCl$_3$) and thionyl chloride (SOCl$_2$).

The compound of general formula:

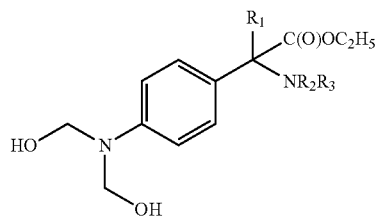

is prepared by reaction of a compound of formula:

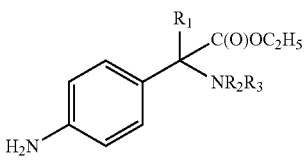

with ethylene oxide.

In particular, U.S. Pat. No. 3,032,584 exemplifies a method for the synthesis of Melphalan which comprises:
a) nitration of D,L-phenylalanine of formula:

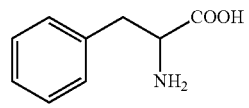 [SMILES: NC(Cc1ccccc1)C(=O)O]

in the presence of nitric acid and sulfuric acid to provide p-nitro-D,L-phenylalanine of formula:

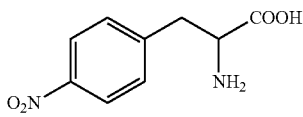 [SMILES: NC(Cc1ccc([N+](=O)[O-])cc1)C(=O)O]

b) esterification of p-nitro-D,L-phenylalanine with phthalic anhydride to provide N-phthaloyl-p-nitrophenylalanine of formula:

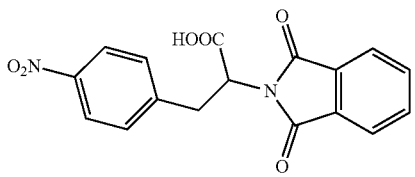 [SMILES: O=C(O)C(Cc1ccc([N+](=O)[O-])cc1)N1C(=O)c2ccccc2C1=O]

c) esterification of the carboxylic acid group of N-phthaloyl-p-nitrophenylalanine with ethanol to provide ethyl N-phthaloyl-p-nitrophenylalanine:

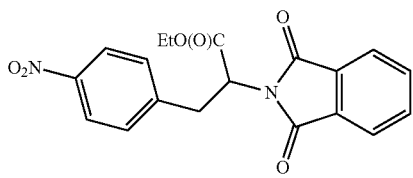

d) hydrogenation of the nitro group of ethyl N-phthaloyl-p-nitrophenylalanine to provide ethyl N-phthaloyl-p-aminophenylalanine:

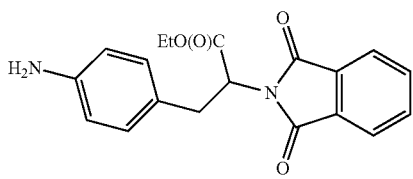

e) reaction of ethyl N-phthaloyl-p-aminophenylalanine with ethylene oxide to provide ethyl-N-phthaloyl-p-bis-(2-hydroxyethyl)-aminophenylalaninate of formula:

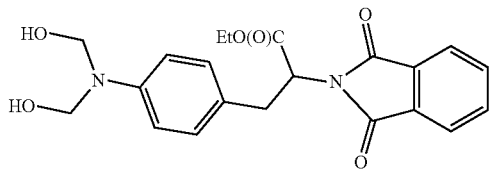

f) chlorination of the —OH groups of ethyl-N-phthaloyl-p-bis-(2-hydroxyethyl)-aminophenylalaninate with POCl$_3$ to provide ethyl-N-phthaloyl-p-bis-(2-chloroyethyl)-aminophenylalaninate of formula:

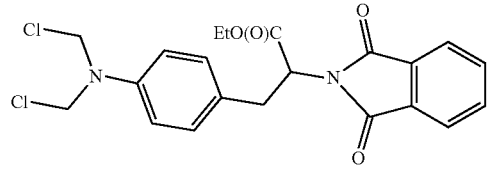

g) treatment of ethyl-N-phthaloyl-p-bis-(2-chloroyethyl)-aminophenylalaninate with concentrated hydrochloric acid and then with a saturated sodium acetate solution to remove the protective groups and obtain (S)-Melphalan (I) (L enantiomer) as hydrochloride salt (mono hydrochloride salt).

U.S. Pat. No. 3,032,585, assigned to National Research Development Corporation, relates to an improvement of the process disclosed in U.S. Pat. No. 3,032,584; the improvement consists in the optical resolution of N-acetyl-p-nitro-D,L-phenylalanine with brucine or p-nitro-N-phthaloyl-D,L-phenylalanine with cinchonidine to respectively obtain N-acetyl-p-nitro-L-phenylalanine and p-nitro-N-phthaloyl-L-phenylalanine that are submitted to synthetic steps similar to those disclosed in U.S. Pat. No. 3,032,584.

CN101100440, assigned to Suzhou Leader Chemical Co LTD, discloses a process for the preparation of Melphalan starting from (S)-4-nitro-phenylalanine ethyl ester, which is protected at the amino group as tert-butoxy carbamate; after the protection reaction, the process is continued in the same way as disclosed in U.S. Pat. No. 3,032,585, with the sole difference that the concentration of hydrochloric acid in the final deprotection reaction of the amino and carboxy moieties is in the range 2M-6M instead of 12M.

WO 2009/117164, assigned to Navinta LLC, discloses a process comprising the hydroxyethylation of the amino group on the phenyl ring of a protected p-aminophenylalanine of formula:

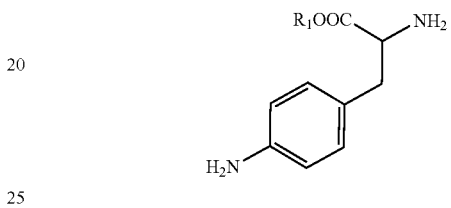

wherein R$_1$ is hydrogen or a C$_1$-C$_6$ straight or branched alkyl chain
under conditions that do not require to protect the amino group of the aminoacid moiety (glycinic NH$_2$).

Thus, the known processes for the synthesis of Melphalan require a hydroxyethylation step of p-amino-L-phenylalanine, either in a protected or a free form. Such step is carried out using ethylene oxide as alkylating agent; however, ethylene oxide is a gas, which presents safety concerns, especially when used on industrial scale.

Therefore, the need is still felt to provide a process for the synthesis of Melphalan that does not require the use of ethylene oxide.

DESCRIPTION OF THE INVENTION

The Applicant has found out that Melphalan (I) can be advantageously synthesized in optically pure L-form through a process comprising the regiospecific bis sulfate-alkylation of the aromatic amino group of a 4-amino-L-phenylalanine.

Thus, in a first aspect, the invention relates to a process for the synthesis of Melphalan (I):

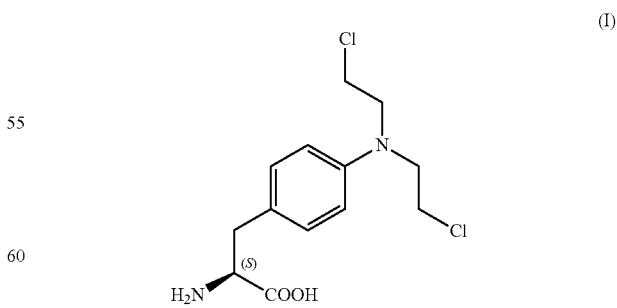

said process comprising the reaction of a 4-amino-L-phenylalanine protected at the carboxy and amino aminoacidic groups with an agent able to convert the aromatic amino group into a group of formula: —N(CH$_2$CH$_2$OS(O)$_n$ O$^-$)$_2$, wherein n is 1 or 2, followed by conversion of the —N(CH$_2$CH$_2$OS(O)$_n$O$^-$)$_2$ group into a —N(CH$_2$CH$_2$Cl)$_2$ group.

In greater detail, the process of the invention comprises the following steps:

a) reaction of a protected 4-amino-L-phenylalanine of formula (II):

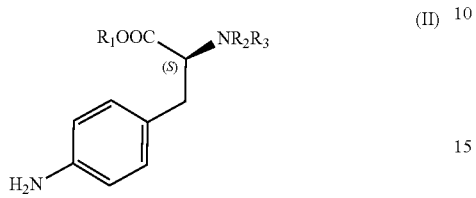
(II)

wherein R$_1$ is a carboxy-protecting group and one of R$_2$ and R$_3$ is hydrogen and the other one is an amino protecting group or R$_2$ and R$_3$, together with the nitrogen atom they are bound to, form an amino-protecting group with 1,3,2-dioxathiolane 2,2-dioxide (also referred to as "ethylene sulfate") of formula (IIIa):

(IIIa)

or with 1,3,2-dioxathiolan-2-oxide (also referred to as ethylene sulfite) of formula (IIIb):

(IIIb)

in the presence of an inorganic base, preferably a carbonate or a bicarbonate, more preferably NaHCO$_3$, KHCO$_3$ or Cs$_2$CO$_3$, to provide a protected 4-(bis-(2-ethylsulfate)-amino-L-phenylalanine or a protected 4-(bis-(2-ethylsulfite)-amino-L-phenylalanine of formula (IV):

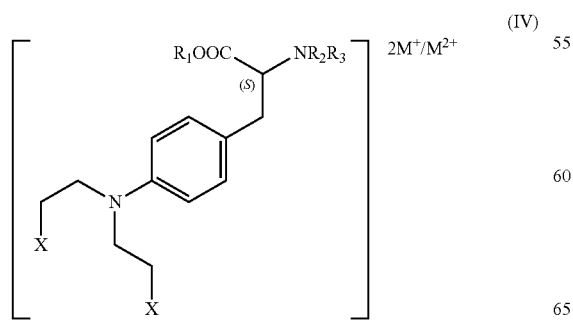
(IV)

wherein R$_1$, R$_2$ and R$_3$ are as defined above, X is OS(O)$_n$O$^-$ wherein n is as defined above, and M$^+$ or M$^{2+}$ is a metallic cation, preferably Na$^+$, K$^+$ or Cs$^+$; Mg$^{2+}$ or Ca$^{2+}$, more preferably Na$^+$, K$^+$ or Cs$^+$, even more preferably Na$^+$.

b) replacement of the sulfate groups or sulfite groups X of compound (IV) with chlorine to provide protected Melphalan of formula (V):

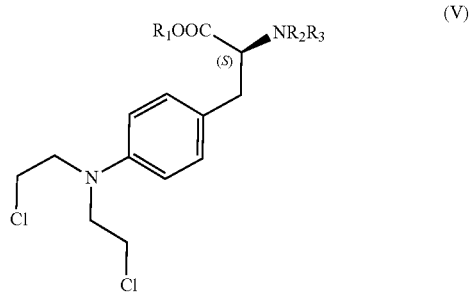
(V)

wherein R$_1$, R$_2$ and R$_3$ are as defined above and c) removal of the protecting groups R$_1$-R$_3$ to provide Melphalan (I).

Preferably, R$_1$ is straight or branched lower alkyl group, more preferably straight or branched C$_1$-C$_6$ alkyl, more preferably ethyl. In one embodiment, R$_2$ is hydrogen and R$_3$ is a group of formula R$_4$—C(O)—, wherein R$_4$ is hydrogen or straight or branched lower alkyl, preferably straight or branched C$_1$-C$_6$ alkyl. In another embodiment, R$_2$ and R$_3$, together with the nitrogen atom they are bound to, represent a group of formula:

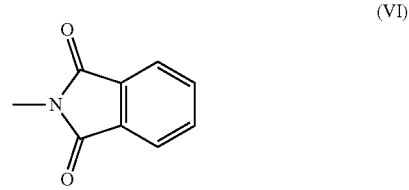
(VI)

In a preferred embodiment of the invention, R$_1$ is ethyl and R$_2$ and R$_3$, together with a nitrogen atom they are bound to, form a group of formula (VI) as defined above.

In a preferred embodiment, a protected 4-amino-L-phenylalanine of formula (II) is reacted with 1,3,2-dioxathiolane 2,2-dioxide (IIIa).

A protected 4-amino-L-phenylalanine (II) can be obtained according to methods known in the art. In particular, a compound of formula (IIa):

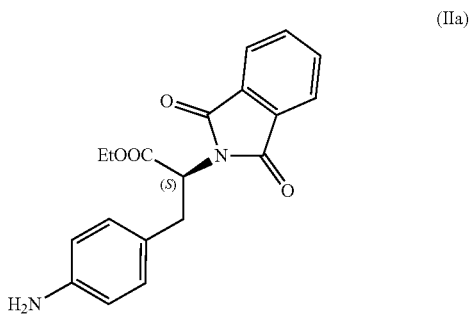
(IIa)

can be obtained as disclosed in Bixue Xu & C., *Bioorganic & Medicinal Chemistry*, 17, (2009), 3118-3125 with regard to the nitration and esterification reactions and in *Tetrahedron Asymmetry*, 22, Issue 2, (2011)185-189 with regard to the protection of the glycinic nitrogen.

Step a) can be carried out in an organic solvent selected from straight or branched $C_5$-$C_{10}$ hydrocarbons, straight or branched halogenated $C_1$-$C_6$ hydrocarbons, linear or cyclic $C_3$-$C_{14}$ ethers or $C_4$-$C_6$ esters, $C_2$-$C_3$ nitriles, dimethylformamide (DMF), dimethylacetamide (DMA) and dimethylsulfoxide (DMSO) at temperatures ranging from 0° C. to 50° C. Conveniently, the reaction is carried out in dichloromethane (DCM) or acetonitrile (ACN) at room temperature (25° C.). At the end of the reaction, the solvent is distilled off and the residue is taken up with an alcohol, preferably with ethanol, thereby obtaining a chemically and optically pure compound (IV).

The compounds of general formula (IV) and their use as intermediates for the synthesis of Melphalan represent a further aspect of the invention. A particularly preferred compound of formula (IV) is compound (IVa), wherein $R_1$ is ethyl, $R_2$ and $R_3$, together with the nitrogen atom they are bound to, represent a group of formula (VI) as defined above, X is —$OS(O)_2O^-$ and $M^+$ and $M^{2+}$ are as defined above:

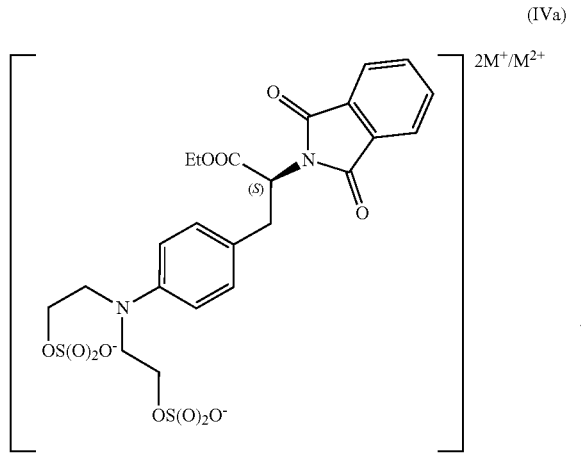

Step b) can be carried out in two different ways.

In a first embodiment [hereinafter "embodiment A"], a compound of formula (IV), preferably the protected 4-(bis-(2-ethylsulfate)-amino-L-phenylalanine (IVa), is first reacted with an inorganic chloride source, such as LiCl, NaCl, KCl, $CaCl_2$, $MgCl_2$ or $BaCl_2$, preferably $CaCl_2$, $MgCl_2$ or $BaCl_2$, even more preferably $BaCl_2$ or $CaCl_2$, thereby obtaining protected 4-(bis-(2-chloroethyl)-amino-L-phenylalanine of formula (V) as defined above, optionally followed by crystallization in a suitable solvent. The reaction with the inorganic chlorine source is carried out in an organic solvent/water mixture, wherein the organic solvent is typically selected from ethyl acetate, dimethylformamide and mixtures of water with tetrahydrofuran, methyltetrahydrofuran, acetonitrile or alcohols at a temperature typically ranging from 20° C. to 60° C. preferably at room temperature.

Thereafter, step c) is carried out by treating protected 4-(bis-(2-chloroethyl)-amino-L-phenylalanine (V) with an acid at pH<1 in water at a temperature ranging from 85 to 115° C., preferably at 110° C., to provide an acidic aqueous solution comprising Melphalan (I) bis-hydrochloride salt. The acid can be inorganic or organic and is typically selected from hydrochloric, sulfuric, citric, methane sulfonic, toluene sulfonic, acetic, perchloric acid or mixtures thereof. Finally, Melphalan can be crystallized by increasing the pH of the aqueous acidic solution; preferably, Melphalan is crystallized as hydrochloride salt (mono hydrochloride salt) by increasing the pH to a value ranging from 5 to about 8.5, preferably from 7.5 to 8.5; pH increase can be achieved using an organic or inorganic base, typically an organic amine or ammonia; according to a preferred embodiment, the base is ammonia.

In a second embodiment [herein after "embodiment B"] step b) is carried out as follows. First, a compound of formula (IV), preferably a protected 4-(bis-(2-ethylsulfate)-amino-L-phenylalanine (IVa) is desulfated using absolute ethanol and sulfuric acid, thereby obtaining protected 4-(bis-(2-hydroxyethyl)-amino-L-phenylalanine of formula (VII):

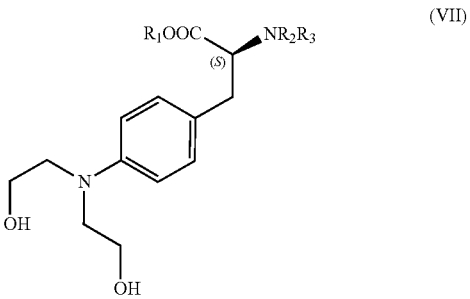

wherein $R_1$, $R_2$ and $R_3$ are as defined above, optionally followed by crystallization in a suitable solvent. The reaction is typically carried out at a temperature ranging from 70° C. to 90° C., conveniently at 80° C., with an amount of sulfuric acid that may range from 0.4 to 2 equivalents with respect to protected 4-(bis-(2-ethylsulfate)-amino-L-phenylalanine (IVa).

The resulting protected 4-(bis-(2-hydroxyethyl)-amino-L-phenylalanine (VII) is then reacted with $POCl_3$ or with $SOCl_2$ to provide a compound of formula (V), which is submitted to step c), as illustrated above. The reaction with $POCl_3$ or with $SOCl_2$ is carried out in an organic solvent, which may be selected from toluene and halogenated hydrocarbons, preferably dichloromethylene or trichloromethylene and at a temperature ranging from room temperature to 110° C. Conveniently, the solvent is toluene and the reaction temperature is room temperature.

The process of the invention is thus advantageous as it avoids the use of ethylene oxide. With specific regard to the use of 1,3,2-dioxathiolane 2,2-dioxide (IIIa), a first advantage is due to the use of 1,3,2-dioxathiolane 2,2-dioxide (IIIa) to perform the bis-alkylation of protected 4-amino-L-phenylalanine (II). Indeed, 1,3,2-dioxathiolane 2,2-dioxide (IIIa) can be used in a considerably lower amount with respect to ethylene oxide (about 2.05 eq with respect to the protected 4-amino-L-phenylalanine (II) vs about 40 eq ethylene oxide to perform the same reaction). 1,3,2-Dioxathiolane 2,2-dioxide (IIIa) can be used in a stoichiometric amount with respect to protected 4-amino-L-phenylalanine (II) and is completely degraded in the reaction. It will also be appreciated that 1,3,2-dioxathiolane 2,2-dioxide (IIIa) is cheaper than ethylene oxide and is not included in the list of toxic gases. Moreover, carrying out the alkylation with 1,3,2-dioxathiolane 2,2-dioxide (IIIa) envisages the use of an organic solvent, which does not promote the hydrolysis of the protective groups on the amino and carboxyl groups of the amino acid moiety.

A second advantage is specifically associated to step b), embodiment A. Indeed, the use of an inorganic chloride as chlorinating agent to perform the chlorination of 4-(bis-(2-ethylsulfate)-amino-L-phenylalanine (IVa) avoids using $SOCl_2$ or $POCl_3$ and, as a consequence, the release of hydrochloric acid and the need to quench the reaction with organic bases, which often leads to the production of toxic gases like $SO_2$. When inorganic chlorides are used, the waste products of the chlorination reaction are inorganic sulfates, whose toxicity is low; moreover, inorganic sulfates are poorly soluble and can be removed from the reaction mixture by simple filtration.

The invention is hereinafter illustrated in greater detail in the following experimental section.

EXPERIMENTAL SECTION

Commercially available reagents and solvents with the following purity degree were used.

L-phenylalanine (purity>99%);
concentrated nitric acid (≥65%);
concentrated sulfuric acid (≥96%);
sodium hydroxide (purity>99%);
absolute ethanol (GC purity>99%);
thionyl chloride (purity>98%);
ethanol (GC purity≥95%), (technical grade);
N-carbethoxyphthalimide (purity≥96%);
acetonitrile (purity≥98%);
anhydrous cesium carbonate (purity≥96%);
10% w/w Pd on activated charcoal;
ethyl acetate (GC purity>95%), (technical grade);
1,3,2-dioxathiolane 2,2-dioxide (purity≥95%);
dichloromethane (amil. stab. purity≥98%);
sodium bicarbonate (purity≥95%);
barium chloride dihydrate (purity≥99%);
sodium chloride (purity≥95%), (technical grade);
HCl 37%, commercial available;
hydrogen was generated in situ using a hydrogen generator.

REFERENCE EXAMPLES—SYNTHESIS OF N-PHTHALIMIDO-4-AMINO-L-PHENYLALANINE ETHYL ESTER (IIa)

Example 1—4-Nitro-L-phenylalanine monohydrate

[Synthesis According to: Bixue Xu & C. Bioorganic & Medicinal Chemistry 17 (2009) 3118-3125]

L-Phenylalanine monohydrate (50 g, 302.7 mmol) was dissolved in $H_2SO_4$ 85% v/v (150 ml) and cooled to 10° C.; the resulting solution was added dropwise and under stirring with a mixture (76.5 ml, 1.4/1.1 vol/vol) of concentrated $HNO_3$ and concentrated $H_2SO_4$ (the mixture was prepared in advance and cooled to room temperature). The resulting reaction solution was stirred for 5 hrs at room temperature, then the pH was adjusted to 2-3 with 40% NaOH and the resulting precipitate was collected by filtration. The wet precipitate was recrystallized from 700 ml water to provide 4-nitro-L-phenylalanine monohydrate as a pale yellow powder (65.9 g, 95%).

Example 2—4-Nitro-L-phenylalanine ethyl ester hydrochloride

[Synthesis According to: Bixue Xu & C. Bioorganic & Medicinal Chemistry 17 (2009) 3118-3125]

4-Nitro-L-phenylalanine (65.9 g, 287.8 mmol) was suspended in 300 ml absolute ethanol ad cooled to 0° C. and the resulting mixture was stirred for 10 min. Thionyl chloride (91.5 ml, 149.9 g, 4.4 eq) was slowly dropped in the reaction mixture under stirring, keeping the internal temperature under 10° C. After completion of the addition, the resulting mixture was heated at 80° C. for 4 hrs, then concentrated to 50 ml and slowly added with ethyl ether (250 ml) at room temperature to provide a white precipitate that was collected by filtration and dried (70.4 g, 95%).

Example 3—N-Phthalimido-4-nitro-L-phenylalanine ethyl ester

[The synthesis was carried out according to the procedure disclosed in: *Tetrahedron Asymmetry*, 22, Issue 2, (2011) 185-189, with the difference that the reaction solvent is acetonitrile instead of water and the inorganic base is cesium carbonate instead of sodium carbonate.]

4-Nitro-L-phenylalanine ethyl ester hydrochloride (60 g, 234.4 mmol) was suspended in 420 ml acetonitrile under stirring at room temperature, then anhydrous $Cs_2CO_3$ (2.0 eq, 152.7 g) was added to the suspension. A solution of N-carbethoxyphthalimide (53.9 g, 1.05 eq) in 240 ml acetonitrile was added during 15 min and the resulting reaction mixture was heated at 40° C. for 24 hrs. The reaction mixture was filtered on a sintered glass filter and the cake was washed with 500 ml of acetonitrile. The mother liquors were concentrated to dryness and the yellow oily residue was crystallized by adding methanol (5 volumes/dry residue), cooling the resulting suspension to 0° C. for an hour and filtering. The wet product was dried at 35° C. under max vacuum for 18 hrs (yield: 61.5 g, 75%).

Example 4—N-Phthalimido-4-nitro-L-phenylalanine ethyl ester

4-Nitro-L-phenylalanine ethyl ester hydrochloride (60 g, 234.4 mmol) was suspended in 480 ml of 2-Methyl-THF under stirring at room temperature, then $KHCO_3$ aqueous solution (10% w/V; 260 ml, 1M) was added to the suspension under stirring.

The phases were left to separated and the aqueous one eliminated. N-carbethoxyphthalimide (51.3 g, 1.0 eq) was added, and the resulting reaction mixture was heated at 55° C. for 6 hrs. After 6 hrs, the temperature was decreased at 20±5° C., and Triethylamine (8.17 ml; 58.6 mmol) was added to the reaction mixture (stirred for 6 hrs). The reaction mixture was washed with 1M HCl (260 ml) and brine (260 ml). The obtained solution was directly used for the preparation of N-Phthalimido-4-amino-L-phenylalanine ethyl ester (IIa)—Example 6

Example 5—N-Phthalimido-4-amino-L-phenylalanine ethyl ester (IIa)

N-phthalimido-4-nitro-L-phenylalanine ethyl ester (50 g, 142.8 mmol) was dissolved in ethyl acetate (500 ml) under stirring at room temperature. When dissolution was complete, 10% Pd on activated charcoal (2 g, 13% mol) was added and the mixture was stirred for 3 hrs under hydrogen atmosphere (0.4 bar) at room temperature. At the reaction completion the catalyst was filtered off and the solution was concentrated to dryness. The resulting crude (46.3 g, 100%) was used without other purification for the further synthetic steps.

Example 6—N-Phthalimido-4-amino-L-phenylalanine ethyl ester (IIa)

N-phthalimido-4-nitro-L-phenylalanine ethyl ester (Solution obtained in Example 4), was kept under stirring at room temperature. An ammonium formate/Phosphoric acid buffer (Ammonium formate: 73.7 g; Phosphoric acid 85%: 22.3 ml in 260 ml of water) was added to the mixture, together with 10% Pd on activated charcoal (4 g). The mixture was stirred for 4.5 hrs at 85° C. At the reaction completion the catalyst was filtered off and the phases separated. The organic one was concentrated to dryness and the crude recrystallised from isopropanol (7 Volumes/weight–10° C.). Yield 94.6%; 52.13 g.

Examples According to the Invention

Example 7 [Step a)]—N-phthalimido-4-(bis-2-ethylsulfate)amino-L-phenylalanine ethyl ester (IVa)

N-Phthalimido-4-amino-L-phenylalanine ethyl ester (IVa) (45 g, 138.9 mmol) was suspended in 315 ml dichloromethane (DCM) or acetonitrile (ACN), then sodium hydrogencarbonate (23.9 g; 284.7 mmol) was added to the suspension at room temperature (RT) and in one portion. 1,3,2-Dioxathiolane 2,2-dioxide (IIIa) (43.1 g; 347.3 mmol) was dissolved in DCM (135 ml) and slowly added to the reaction mixture (1 h); the resulting reaction mixture was stirred at RT for 18 hrs. Upon completion of the reaction, DCM was distilled off under vacuum and replaced with absolute ethanol (450 ml). The solid precipitate was recovered by filtration under nitrogen atmosphere and dried at 40° C. for 24 hrs (yield: 77.0 g; 90%).

Example 8 [Step b), Embodiment A]—N-phthalimido-4-(bis-2-chloroethyl) amino-L-phenylalanine ethyl ester N-phthalimido-4-(bis-2-ethylsulfate)-amino-L-phenylalanine (70 g; 113.6 mmol) was suspended in ethyl acetate previously saturated with water at RT (700 ml), then added with dimethylformamide (35 ml). The mixture was stirred at RT for 20 min, then barium chloride dihydrate (83.2 g; 340.8 mmol) was added in two consecutive portions (5 min.). The reaction was stirred at RT for 18 hrs and then filtered on a sintered glass filter to remove solid sulfates. The ethyl acetic organic phase was washed twice with brine (2×200 ml) and dried under vacuum till dryness. Yield: 46.8 g; 92%.

Example 9 [Step b), Embodiment A]—N-phthalimido-4-(bis-2-chloroethyl) amino-L-phenylalanine ethyl ester N-phthalimido-4-(bis-2-ethylsulfate)-amino-L-phenylalanine (70 g; 113.6 mmol) was suspended in acetonitrile (700 ml). Anhydrous calcium chloride was added, and the mixture was stirred at 60° C. for 13 hrs and then filtered on a sintered glass filter to remove solid sulfates. The solvent was removed under vacuum. Yield: 49.8 g; 98%.

Example 10 [Step b), Embodiment B]—N-Phthalimido-4-(bis-2-hydroxyethyl) amino-L-phenylalanine ethyl ester (Va)

N-phthalimido-4-(bis-2-ethylsulfate)-amino-L-phenylalanine (70 g; 113.6 mmol) was suspended in absolute ethanol (700 ml) at RT. Concentrated $H_2SO_4$ (12.1 ml; 227.2 mmol) was slowly dropped in the reaction mixture under stirring. When the addition was completed, the mixture was heated at 80° C. for an hour. Ethanol was removed by distillation under vacuum and the oily residue was dissolved in methylene chloride (300 ml). The resulting organic solution was washed twice with a sodium hydrogencarbonate solution 5% w/vol, dried over magnesium sulfate end evaporated under vacuum till dryness. The oily residue was recrystallized with ethyl acetate (yield 45.9 g; 98%).

Example 11 [Step c, Embodiment B]—N-phthalimido-4-(bis-2-chloroethyl) amino-L-phenylalanine ethyl ester (VIIa) from N-phthalimido-4-(bis-2-hydroxyethyl) amino-L-phenylalanine ethyl ester (Va)

N-phthalimido-4-(bis-2-hydroxyethyl) amino-L-phenylalanine ethyl ester (Va) (50 g, 121.4 mmol) was dissolved in toluene (500 ml). Freshly distilled $POCl_3$ (37.2 g; 22.7 ml, 242.8 mmol) was slowly added in the reaction mixture at RT (1 h). The reaction was heated at 110° C. for 1 h, then the solvent was removed under vacuum (yield: 48.9 g; 90%).

Example 12 [Step c)]—Melphalan (I) Hydrochloride Salt

N-phthalimido-4-(bis-2-chloroethyl) amino-L-phenylalanine ethyl ester (VIIa) (50 g; 111.6 mmol) was dissolved in hydrochloric acid 37% w/w (200 ml) then heated under reflux for 24 hrs. The reaction mixture was cooled at room temperature and stirred at 20-25° C. for 8 hrs. The solid residue (phthalic acid) was removed by filtration and the mother liquor was added with a solution of ammonia (33% w/w, 16.1 M) until reaching a pH in the range between 8.0 to 8.4 at 0° C. The resulting solid Melphalan was filtered and re-dissolved in 1M HCl (120 ml) at 0° C., then treated with 1M ammonia until reaching a pH in the range between 8.0 to 8.4. The solid precipitate was filtered and dried under vacuum at 40° C. for 24 hrs (23.6 g; 90%).

The invention claimed is:

1. A compound of formula (IV):

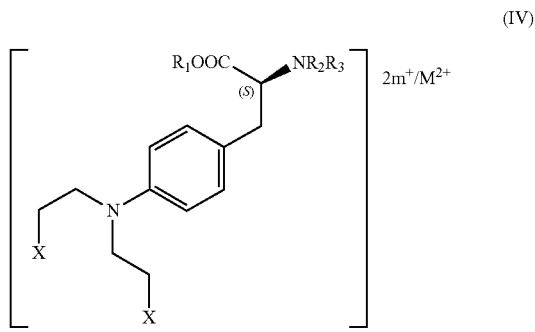

wherein $R_1$ is a carboxy-protecting group and one of $R_2$ and $R_3$ is hydrogen and the other one is an amino protecting group or $R_2$ and $R_3$ together with the nitrogen atom they are bound to form an amino-protecting group, X is $-OS(O)_nO^-$, wherein n is 1 or 2, and $M^+$ or $M^{2+}$ is a metallic cation.

2. A compound according to claim 1 wherein $R_1$ is ethyl, and $R_2$ and $R_3$, together with the nitrogen atom they are bound to, represent a group of formula (VI):

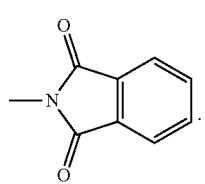
(VI)
3. A compound according to claim 1 wherein X is —OS(O)$_2$O$^-$.
* * * * *